US012583805B2

(12) United States Patent
Barias

(10) Patent No.: US 12,583,805 B2
(45) Date of Patent: Mar. 24, 2026

(54) CO-PRODUCTION OF HIGH PURITY ISOBUTYLENE AND HIGH PURITY ISOOCTENE

(71) Applicant: LUMMUS TECHNOLOGY LLC, Houston, TX (US)

(72) Inventor: Rosette Barias, Houston, TX (US)

(73) Assignee: Lummus Technology LLC, Houston, TX (US)

( * ) Notice: Subject to any disclaimer, the term of this patent is extended or adjusted under 35 U.S.C. 154(b) by 224 days.

(21) Appl. No.: 18/638,036

(22) Filed: Apr. 17, 2024

(65) Prior Publication Data

US 2024/0351963 A1 Oct. 24, 2024

Related U.S. Application Data

(60) Provisional application No. 63/497,236, filed on Apr. 20, 2023.

(51) Int. Cl.
*C07C 2/06* (2006.01)
*B01D 3/00* (2006.01)
*B01J 19/24* (2006.01)
*C07C 1/22* (2006.01)
*C07C 2/86* (2006.01)
*C07C 7/09* (2006.01)

(52) U.S. Cl.
CPC ................ *C07C 2/06* (2013.01); *B01D 3/009* (2013.01); *B01J 19/245* (2013.01); *C07C 1/22* (2013.01); *C07C 7/09* (2013.01); *C07C 2/86* (2013.01); *C07C 2/862* (2013.01); *C07C 2/864* (2013.01)

(58) Field of Classification Search
CPC .... C07C 2/06; C07C 1/22; C07C 7/09; C07C 2/86; C07C 2/862; C07C 2/864; C07C 1/20; C07C 2/08; C07C 41/06; B01D 3/009; B01D 3/40; B01J 19/245
See application file for complete search history.

(56) References Cited

U.S. PATENT DOCUMENTS

| | | | |
|---|---|---|---|
| 6,660,898 B1 * | 12/2003 | Pyhalahti | C10G 50/00 585/329 |
| 8,188,327 B1 | 5/2012 | Bakshi | |
| 9,422,205 B2 | 8/2016 | Brianti et al. | |
| 11,505,512 B2 | 11/2022 | Almering et al. | |
| 2008/0081939 A1 | 4/2008 | Bakshi | |
| 2012/0010451 A1 | 1/2012 | Di Girolamo et al. | |

OTHER PUBLICATIONS

International Search Report issued in Application No. PCT/US2024/024893 mailed on Aug. 7, 2024 (3 pages).
(Continued)

*Primary Examiner* — Ali Z Fadhel
(74) *Attorney, Agent, or Firm* — Osha Bergman Watanabe & Burton LLP

(57) ABSTRACT

Systems and processes for the production of a high purity isobutylene stream, a high purity isooctene stream or for the co-production of a high purity isobutylene and a high purity isooctene. The systems and processes advantageously process mixed C4 hydrocarbon streams via etherification, back cracking, isomerization, and/or dimerization, along with various separation systems, to produce the desired high purity streams.

18 Claims, 6 Drawing Sheets

(56) References Cited

OTHER PUBLICATIONS

Written Opinion Report issued in Application No. PCT/US2024/024893 mailed on Aug. 7, 2024 (4 pages).
International Preliminary Report on Patentability issued in Application No. PCT/US2024/024893, mailed on Oct. 16, 2025 (5 pages).
Notification Concerning Transmittal of International Preliminary Report on Patentability issued in Application No. PCT/US2024/024893, mailed on Oct. 30, 2025 (1 pages).

* cited by examiner

Figure 6

CO-PRODUCTION OF HIGH PURITY ISOBUTYLENE AND HIGH PURITY ISOOCTENE

FIELD OF THE DISCLOSURE

Embodiments of the present disclosure generally relate to systems and processes for the co-production of high purity isooctene and high purity isobutylene.

BACKGROUND

High purity isobutylene is used as a raw material for the production of butyl rubber, PIB (polyisobutylene), MMA (methyl methacrylate) and is usually produced from the commercially proven MTBE decomposition process. High purity isooctene is used as a raw material for the production of octylphenol resins used as tackifiers in radial tires, octylated diphenylamine stabilizers for lubricants and rubbers, isononyl derivatives used to produce polymerization initiators and compressor fluids, and as co-monomer in the production of elastomers and hydrocarbon resins, or as chain stop agent for polycarbonate resins.

SUMMARY OF THE CLAIMED EMBODIMENTS

Embodiments herein relate to the production of high purity isobutylene and high purity diisobutylene (a.k.a. isooctene or a mixture of 2,4,4-trimethyl-1-pentene and 2,4,4-trimethyl-2-pentene) including olefin dimerization steps, etherification, ether decomposition or a combination of butene isomerization and hydrogenation. Embodiments herein also contemplate use of several dimerization moderators, such as C1 to C4 alcohols, other oxygenates such as ETBE, ESBE, MTBE, MSBE, water and/or ethylene glycol. The scheme can be flexible in producing both high purity isobutylene, high purity isooctene, or just high purity isooctene.

In one aspect, embodiments disclosed herein relate to a process for co-production of high purity isobutylene and high purity isooctene. The process includes feeding ethanol and mixed C4 hydrocarbon to an ETBE conversion unit, the mixed C4 feed containing a mixture of hydrocarbons including 1-butene, 2-butene, n-butane, isobutane, and isobutylene. In the ETBE conversion unit, the isobutylene is catalytically reacted with the ethanol to form ethyl tert butyl ether, producing an ETBE reaction effluent which is recovered from the reactor and separated to recover a first fraction comprising the ethyl tert butyl ether and a second fraction comprising 1-butene, 2-butene, isobutane, and n-butane. The first fraction comprising the ethyl tert butyl ether is then fed to an ETBE decomposition unit. In the ETBE decomposition unit, the ethyl tert butyl ether is decomposed to form a decomposition reaction effluent comprising isobutylene, ethanol, and unreacted ethyl tert butyl ether, which is then separated to recover an isobutylene fraction, comprising 95 wt % or greater isobutylene, and a first oxygenate fraction comprising the ethanol and unreacted ethyl tert butyl ether. A first portion of the isobutylene fraction is recovered as a high purity isobutylene product fraction. A second portion of the isobutylene fraction is fed to an isobutylene dimerization unit. A portion of the first fraction comprising ethyl tert butyl ether, a portion of the first oxygenate fraction, or both, are also fed to the isobutylene dimerization unit as a reaction moderator. In the isobutylene dimerization unit, the isobutylene is dimerized to form a dimerization reaction effluent comprising isooctene, reaction moderator, and byproduct isobutylene trimers and oligomers, which is then separated to recover a heavy fraction comprising isooctene, the byproduct isobutylene trimers and oligomers, ethyl tert butyl ether, and ethanol and a lights fraction comprising isobutylene and ethanol. The heavy fraction is fed to an oxygenate splitter for separating the heavy fraction to recover a first dimerization product fraction comprising isooctene and the byproduct isobutylene trimers and oligomers and a second dimerization product fraction comprising reaction moderator. The first dimerization product fraction is fed to a DIB purification unit, in which the first dimerization product fraction is separated to recover an isooctene fraction, comprising 95 wt % or greater isooctene, and a byproduct fraction comprising the isobutylene trimers and oligomers.

In another aspect, embodiments disclosed herein relate to a process for co-production of high purity isobutylene and high purity isooctene. The process includes feeding methanol and mixed C4 hydrocarbon to a MTBE conversion unit, the mixed C4 feed containing a mixture of hydrocarbons including 1-butene, 2-butene, n-butane, isobutane, and isobutylene. In the MTBE conversion unit, isobutylene is catalytically reacted with methanol to form methyl tert butyl ether, recovering an MTBE reaction effluent, which is separated to recover a first fraction comprising the methyl tert butyl ether and a second fraction comprising 1-butene, 2-butene, isobutane, and n-butane. The first fraction comprising the methyl tert butyl ether is then fed to an MTBE decomposition unit. In the MTBE decomposition unit, methyl tert butyl ether is decomposed to form a decomposition reaction effluent comprising isobutylene, methanol, and unreacted methyl tert butyl ether, which is then separated to recover an isobutylene fraction, comprising 95 wt % or greater isobutylene, and a first oxygenate fraction comprising the methanol and unreacted methyl tert butyl ether. A first portion of the isobutylene fraction is recovered as a high purity isobutylene product fraction; a second portion of the isobutylene fraction is fed to an isobutylene dimerization unit. A portion of the first fraction comprising methyl tert butyl ether, a portion of the first oxygenate fraction, or both, is also fed to the isobutylene dimerization unit as a reaction moderator. In the isobutylene dimerization unit, the isobutylene is dimerized to form a dimerization reaction effluent comprising isooctene, reaction moderator, and byproduct isobutylene trimers and oligomers, which is then separated to recover a heavy fraction comprising isooctene, the byproduct isobutylene trimers and oligomers, methyl tert butyl ether, and methanol and a lights fraction comprising isobutylene and methanol. The heavy fraction is then separated in an oxygenate splitter to recover a first dimerization product fraction comprising isooctene and the byproduct isobutylene trimers and oligomers and a second dimerization product fraction comprising reaction moderator. The first dimerization product fraction is fed to a DIB purification unit, in which the first dimerization product fraction is separated to recover an isooctene fraction, comprising 95 wt % or greater isooctene, and a byproduct fraction comprising the isobutylene trimers and oligomers.

In another aspect, embodiments disclosed herein relate to a process for co-production of high purity isobutylene and high purity isooctene. The process includes feeding a mixed C4 stream, comprising a mixture of hydrocarbons including 1-butene, 2-butene, n-butane, isobutane, and isobutylene, to a catalytic separation unit. In the catalytic separation unit, a portion of the 1-butene is converted to 2-butene and the mixture of hydrocarbons is separated to recover a first overheads fraction comprising 1-butene, isobutane, and isobutene and a bottoms fraction comprising n-butane and 2-butene. A portion of the first overheads fraction is recovered as a high purity isobutylene product fraction comprising at least 95 wt % isobutylene. The process also includes feeding an alcohol, selected from ethanol or methanol, and a second portion of the first overheads fraction to an etherification conversion unit. In the etherification conversion unit, alcohol and isobutylene are reacted to form an alkyl tert butyl ether, recovering an etherification reaction effluent comprising alkyl tert butyl ether and alcohol. The etherification reaction effluent is fed to an isobutylene dimerization unit as a reaction moderator. A second portion of the first overheads fraction is also fed to the isobutylene dimerization unit. In the isobutylene dimerization unit, the isobutylene is dimerized to form a dimerization reaction effluent comprising isooctene, reaction moderator, and byproduct isobutylene trimers and oligomers, and the dimerization reaction effluent is separated to recover a heavy fraction comprising isooctene, the byproduct isobutylene trimers and oligomers, alkyl tert butyl ether, and alcohol and a lights fraction comprising isobutylene and alcohol. The heavy fraction is fed to an oxygenate splitter to recover a first dimerization product fraction comprising isooctene and the byproduct isobutylene trimers and oligomers and a second dimerization product fraction comprising reaction moderator. Further, the first dimerization product fraction is fed to a DIB purification unit; in which the first dimerization product fraction is separated to recover an isooctene fraction, comprising 95 wt % or greater isooctene, and a byproduct fraction comprising the isobutylene trimers and oligomers.

In another aspect, embodiments disclosed herein relate to systems for co-production of high purity isobutylene and high purity isooctene. The systems include an etherification unit (ETBE or MTBE conversion units), a decomposition unit, an isobutylene dimerization unit, an oxygenate splitter, and a DIB purification unit.

In embodiment systems utilizing ethanol, the system may include one or more flow conduits for providing ethanol and mixed C4 hydrocarbon to an ETBE conversion unit, the mixed C4 feed containing a mixture of hydrocarbons including 1-butene, 2-butene, n-butane, isobutane, and isobutylene. The ETBE conversion unit includes one or more reactors configured for catalytically reacting the isobutylene with the ethanol to form ethyl tert butyl ether, recovering an ETBE reaction effluent, and a separation system configured for separating the ETBE reaction effluent to recover a first fraction comprising the ethyl tert butyl ether and a second fraction comprising 1-butene, 2-butene, isobutane, and n-butane. A flow line is provided for feeding the first fraction comprising the ethyl tert butyl ether to an ETBE decomposition unit. The ETBE decomposition unit includes one or more reactors configured for decomposing ethyl tert butyl ether to form a decomposition reaction effluent comprising isobutylene, ethanol, and unreacted ethyl tert butyl ether, and a separation system configured for separating the reaction effluent to recover an isobutylene fraction, comprising 95 wt % or greater isobutylene, and a first oxygenate fraction comprising the ethanol and unreacted ethyl tert butyl ether. A flow line is provided for recovering a first portion of the isobutylene fraction as a high purity isobutylene product fraction, and also provided is a flow line for feeding a second portion of the isobutylene fraction to an isobutylene dimerization unit. Further, a flow line is provided for feeding a portion of the first fraction comprising ethyl tert butyl ether, a portion of the first oxygenate fraction, or both, to the isobutylene dimerization unit as a reaction moderator. The isobutylene dimerization unit includes one or more reactors configured for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, ethyl tert butyl ether, and ethanol and a lights fraction comprising isobutylene and ethanol. The oxygenate splitter is configured for separating the heavy fraction to recover a first dimerization product fraction comprising isooctene and the byproduct isobutylene trimers and oligomers and a second dimerization product fraction comprising reaction moderator. A flow line is fluidly connected for feeding the first dimerization product fraction to a DIB purification unit. And, the DIB purification unit includes a separation system for separating the first dimerization product fraction to recover an isooctene fraction, comprising 95 wt % or greater isooctene, and a byproduct fraction comprising the isobutylene trimers and oligomers.

Similarly, for systems utilizing methanol, the system may include similar unit operations as described above with respect to ethanol, although configured slightly differently to account for the differences in use and recovery of the methanol as compared to ethanol and the associated byproducts.

The systems of such embodiments include one or more flow conduits for providing methanol and mixed C4 hydrocarbon to a MTBE conversion unit, the mixed C4 feed containing a mixture of hydrocarbons including 1-butene, 2-butene, n-butane, isobutane, and isobutylene. The MTBE conversion unit includes one or more reactors configured for catalytically reacting isobutylene with methanol to form methyl tert butyl ether, recovering an MTBE reaction effluent, and a separation system for separating the MTBE reaction effluent to recover a first fraction comprising the methyl tert butyl ether and a second fraction comprising 1-butene, 2-butene, isobutane, and n-butane. A flow line is provided for feeding the first fraction comprising the methyl tert butyl ether to an MTBE decomposition unit. The MTBE decomposition unit includes one or more reactors for decomposing methyl tert butyl ether to form a decomposition reaction effluent comprising isobutylene, methanol, and unreacted methyl tert butyl ether, and a separation system configured for separating the reaction effluent to recover an isobutylene fraction, comprising 95 wt % or greater isobutylene, and a first oxygenate fraction comprising the methanol and unreacted methyl tert butyl ether. A flow line is provided for recovering a first portion of the isobutylene fraction as a high purity isobutylene product fraction; another flow line is provided for feeding a second portion of the isobutylene fraction to an isobutylene dimerization unit. Further, a flow line is provided for feeding a portion of the first fraction comprising methyl tert butyl ether, a portion of the first oxygenate fraction, or both, to the isobutylene dimerization unit as a reaction moderator. The isobutylene dimerization unit includes one or more reactors for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, methyl tert butyl ether, and methanol and a lights fraction comprising isobutylene and methanol. The oxygenate splitter is configured for separating the heavy fraction to recover a first dimerization product fraction comprising isooctene and the byproduct isobutylene trimers and oligomers and a second dimerization product fraction comprising reaction moderator. A flow line is provided for feeding the first dimerization product fraction to a DIB purification unit, which includes a separation system for separating the first dimerization product fraction to recover an isooctene fraction, comprising 95 wt % or greater isooctene, and a byproduct fraction comprising the isobutylene trimers and oligomers.

In another aspect, embodiments disclosed herein relate to a system for co-production of high purity isobutylene and high purity isooctene. The system includes one or more flow lines for feeding a mixed C4 stream, comprising a mixture of hydrocarbons including 1-butene, 2-butene, n-butane, isobutane, and isobutylene, to a catalytic separation unit. The catalytic separation unit includes a catalytic distillation column configured for concurrently converting a portion of the 1-butene to 2-butene and separating the mixture of hydrocarbons to recover a first overheads fraction comprising 1-butene, isobutane, and isobutene and a bottoms fraction comprising n-butane and 2-butene. A flow line is provided for recovering a portion of the first overheads fraction as a high purity isobutylene product fraction comprising at least 95 wt % isobutylene. One or more flow lines are provided for feeding an alcohol, selected from ethanol or methanol, and a second portion of the first overheads fraction to an etherification conversion unit. The etherification conversion unit includes one or more reactors for reacting alcohol and isobutylene to form an alkyl tert butyl ether, recovering an etherification reaction effluent comprising alkyl tert butyl ether and alcohol. A flow line is provided for feeding the etherification reaction effluent to an isobutylene dimerization unit as a reaction moderator; a flow line is also provided for feeding a second portion of the first overheads fraction to the isobutylene dimerization unit. The isobutylene dimerization unit includes one or more reactors for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, alkyl tert butyl ether, and alcohol and a lights fraction comprising isobutylene and alcohol. The oxygenate splitter is configured for separating the heavy fraction to recover a first dimerization product fraction comprising isooctene and the byproduct isobutylene trimers and oligomers and a second dimerization product fraction comprising reaction moderator. Further, a flow line is provided for feeding the first dimerization product fraction to a DIB purification unit. The DIB purification unit includes a separation system for separating the first dimerization product fraction to recover an isooctene fraction, comprising 95 wt % or greater isooctene, and a byproduct fraction comprising the isobutylene trimers and oligomers.

While outlined above for co-production of high purity isooctene and high purity isobutylene, embodiments herein contemplate feeding a majority or all of the high purity isobutylene for production of high purity isooctene as outlined above and as described further hereinbelow.

Other aspects and advantages will be apparent from the following description and the appended claims.

BRIEF DESCRIPTION OF DRAWINGS

FIG. 6 illustrates a simplified block flow diagram of an etherification unit according to one or more embodiments disclosed herein.

DETAILED DESCRIPTION

Figure 1:
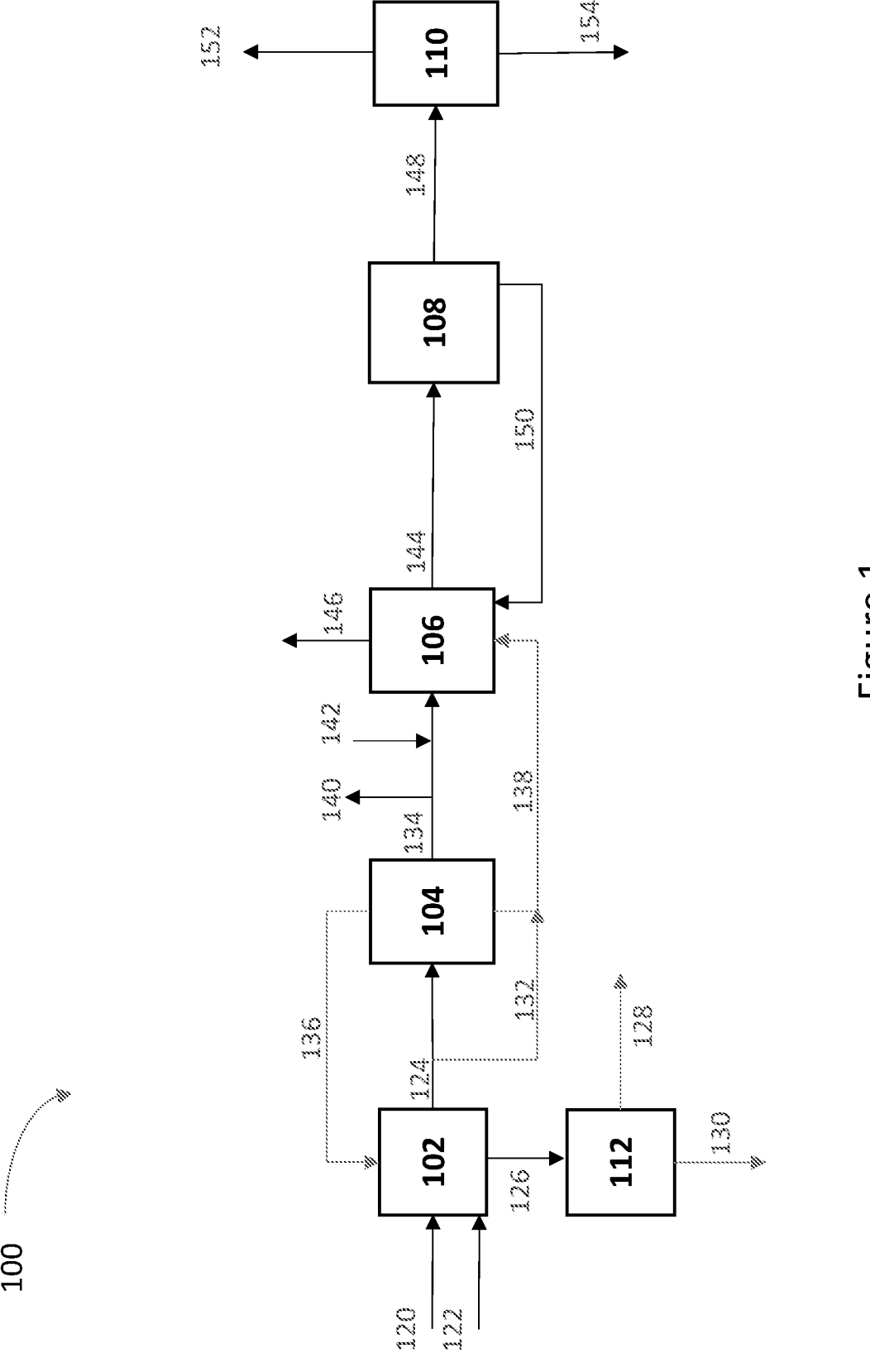
FIGS. 1-3 illustrate simplified process flow diagrams of systems for co-producing high purity isobutene and high purity isooctene according to one or more embodiments disclosed herein.

Embodiments of the present disclosure generally relate to systems and processes for the co-production of high purity isooctene and high purity isobutylene. More specifically, embodiments herein are directed toward the production of high purity isobutylene and high purity isooctene from mixed C4 streams.

Alcohol feeds useful in embodiments herein include methanol or ethanol. In other embodiments, alcohol feeds may include propanol or butanol, among other C3 and C4 alcohols.

Various upstream production processes may be used to generate C4 streams, such as fluid catalytic cracking (FCC) units, resid fluid catalytic cracking units (RFCC), steam crackers, pyrolysis units (thermal cracking with or without steam), and various other methods of producing mixed C4s. The mixed C4 streams produced from these units may include isobutene, isobutane, 1-butene, 2-butene, n-butane, and butadienes, among other components.

While producing similar chemical compounds, these upstream C4 producing systems result in streams having different compositional mixtures of the various C4 compounds. For example, FCC or RFCC mixed C4s may have a much higher concentration of isobutane (>20 wt % or >25 wt %, for example) than a Raffinate-1 recovered from a steam cracker butadiene production process (<5 wt % or <3 wt % isobutane, for example). At the same time, the concentration of isobutylene in the FCC/RFCC C4s is much lower than for steam cracker C4s, (such as <25 or 30 wt % for RFCC vs. >35 or 40 wt % for steam cracker C4s). Likewise, each (FCC/RFCC vs. steam cracker) may have a difference in the concentration of 1-butene (such as less than 20 or 15 wt % vs. greater than 35 or 40 wt %). Further, the diene content of the FCC/RFCC mixed C4s is much higher than for the steam cracker Raffinate-1 (such as 0.3 wt % or 3,000 ppmw vs. 40 ppmw). Embodiments herein may produce high purity isobutylene and high purity isooctene from any of these various streams or mixtures of two or more of these streams.

In general, embodiments herein first convert the mixed C4s with isobutylene into oxygenates via etherification and then decompose the oxygenates to a high purity isobutylene (HPIB) stream and a C1-C2 alcohol. The HPIB is then diluted by a C4 paraffin to control the exothermic reactions in dimerization. The oxygenates from the decomposition step along with the recovered oxygenates from the downstream splitter are used as reaction moderators to control the oligomerization reactions and for better selectivity to high purity isooctene (HPDIB). A variation in the HPIB preparation is through hydroisomerization.

In a first aspect, for example, mixed C4s are reacted with ethanol to produce ETBE, which is then decomposed (back-cracked) to produce high purity isobutylene as part of the feed preparation for the high purity isooctene production steps. For a fully integrated scheme, all the HPIB produced is diluted with a C4 paraffin that is envisioned as a semi-closed loop system, depending on the amount of HPIB that gets produced. The recycle paraffin forms an azeotrope with ethanol (in the case with ETBE, for example) that gets sent back to the dimerization as feed, and during normal operation it is expected that the diluent will get reduced (make-up only). The ethanol that goes with the diluent will also act as an additional moderator for the dimerization process. From the backcracking step, an oxygenate purge comprising of ETBE, some ESBE (depending on the n-butenes that reacted), TBA, ethanol, DEE and water are also sent to the dimerization step as reaction moderators. A slip stream of the ETBE product from the etherification step may be needed depending on the oxygenate purge from the back-cracking step. In the dimerization step, HPIB is diluted with C4 paraffins and oxygenates. Since the HPIB produced has very low linear butenes present, it is expected that the dimerization step will be selective in producing 2,4,4-trimethyl-1 pentene/2-pentene (244TM1P and 244TM2P) with less than 1 wt % C8 codimers such as dimethylhexene. The C8, C12+, oxygenates are then sent to a purification section wherein the oxygenates, C12+ and main DIB product are separated. The oxygenates are then recycled to the dimerization step as moderators. An oxygenates purge in the dimerization step may or may not be needed depending on the management and closure of the oxygenates that are needed in the dimerization reaction. A similar embodiment is envisioned where the alcohol used is methanol, resulting in methyl tert butyl ether (MTBE) and MTBE decomposition to form high purity isobutylene, among the other reaction and separation steps.

In a second aspect, for example, mixed C4s are sent to a catalytic deisobutenizer. In the catalytic section of the column, the butene-1 component in the feed is isomerized to butene-2 for case of separation from the isobutylene and isobutane in the mixed feed. A small amount of hydrogen is fed in the distillation column to manage the hydroisomerization reactions in the catalytic section. The overhead is expected to be composed of isobutane, isobutylene, and a small amount of butene-1. The bottoms is composed of n-butane and the rest of the butene-2 along with any heavies that may be present in the mixed C4 feedstock. The overhead is then split into two streams. One of the streams is the main feed to the dimerization step and the other stream is for the production of the oxygenates, in this case, ETBE from the reaction of ethanol. The ETBE reaction step can be inside the dimerization unit. Another variation of this dimerization step is comprised of an ETBE reactor (only etherification) followed by the dimerization unit. The etherification step depends on the requirement in dimerization. Similar to the first aspect described above, the dimerization step will involve dilution by an external C4 paraffin stream and the splitting and purification sections to produce the oxygenate streams and the main high purity DIB product. Likewise, a similar reaction/separation scheme may employ methanol as the alcohol.

In one or more embodiments of the present disclosure, the purity of the high purity isobutylene produced may be from a lower amount of any of 85%, 86%, 87%, 88%, 89%, 90%, 91%, 92%, 93%, 94%, 95%, 96%, 97%, or 98% on a wt % basis, to an upper limit of any of 90%, 91%, 92%, 93%, 94%, 95%, 98%, 98.5, 99.0, 99.5, 99.8 or 99.9% on a wt % basis, where any lower limit may be combined with any mathematically compatible upper limit. For example, the purity of the isobutylene produced may be at least 95%, at least 98%, at least 99%, or at least 99.5%, on a wt % basis.

In one or more embodiments of the present disclosure, the purity of the high purity isooctene produced may be from a lower amount of any of 85%, 86%, 87%, 88%, 89%, 90%, 91%, 92%, 93%, 94%, 95%, 96%, 97%, or 98% on a wt % basis, to an upper limit of any of 90%, 91%, 92%, 93%, 94%, 95%, 98%, 98.5, 99.0, 99.5, 99.8 or 99.9% on a wt % basis, where any lower limit may be combined with any mathematically compatible upper limit. For example, the purity of the isooctene produced may be at least 95%, at least 98%, at least 99%, or at least 99.5%, on a wt % basis.

Referring now to FIG. 1, a simplified process flow diagram of a system 100 for producing high purity isobutylene and high purity isooctene according to embodiments herein is illustrated. System 100 may include primary unit operations including an MTBE conversion unit 102, a MTBE decomposition unit 104, an isobutylene dimerization unit 106, an oxygenate splitter 108, a diisobutylene purification zone 110, and an optional C4 separation zone 112. Each of these units may include, among other components, one or more of feed pretreatment equipment (filters, adsorbent beds, etc.), storage tanks, one or more reactors in series and/or parallel, separation units, which may include distillation columns, extractive distillation columns, flash drums, and/or strippers, and other components such as valves, pumps, controllers, overhead condensation systems (condensers, heat exchangers, drums, etc.), reboilers, etc. Not all units include each of these equipment. Further, while these components are not illustrated in the simplified process flow diagram, one skilled in the art can readily appreciate and understand the process flow and how such equipment may be incorporated as outlined in the following description.

Methanol 120 and mixed C4 hydrocarbon stream 122 are fed to the MTBE conversion unit, which includes one or more reactors or catalytic distillation columns containing an etherification catalyst. The mixed C4 feed may include, for example, a mixture of hydrocarbons including 1-butene, 2-butene, n-butane, isobutane, and isobutylene. In the MTBE conversion unit, the feeds are contacted with the etherification catalyst at appropriate conditions for catalytically reacting isobutylene with methanol to form methyl tert butyl ether. An MTBE reaction effluent is recovered from the reaction zone(s), and the MTBE reaction effluent is then separated to recover a first fraction 124 comprising the methyl tert butyl ether and a second fraction 126 comprising 1-butene, 2-butene, isobutane, and n-butane. In addition to recovering the MTBE and C4 products, MTBE conversion zone 102 may further include water wash columns, extractive distillation columns, and/or other separators for separating unreacted methanol from the MTBE product, where the methanol may be returned to the reactor for continued use in producing MTBE.

If it is desired to further process and separate the remaining C4 components in the second fraction, such as to recover 2-butene or isobutane, second fraction 126 may be fed to C4 separation zone 112. C4 separation zone 112 may include, for example, a distillation column or superfractionator to separate a heavy C4 fraction 128, including n-butane and 2-butene, from a light C4 fraction 130, including 1-butene, isobutane, and any unreacted isobutylene from the etherification reactor. In other embodiments, C4 separation zone 112 may include a catalytic deisobutenizer, which may include a positional isomerization catalyst zone for converting 1-butene to 2-butene and distillation structure or trays for separating a light C4 fraction 130, including isobutane and any unreacted isobutylene, from a heavy C4 fraction, including the 2-butene and n-butane.

First fraction 124, which includes the methyl tert butyl ether produced in the etherification reactor, is then fed to an MTBE decomposition unit 104. For startup or as make-up oxygenate reaction modifier (selectivator), a portion 132 of the first fraction may be routed to isobutylene dimerization unit 106.

In the MTBE decomposition unit, the methyl tert butyl ether is decomposed (back cracked) to form a decomposition reaction effluent comprising isobutylene, methanol, and unreacted methyl tert butyl ether. The reaction effluent is then separated to recover an isobutylene fraction 134, which may be a high purity isobutylene stream, such as containing 95 wt % or greater isobutylene, and a first oxygenate fraction 136, which may include the methanol resulting from the back cracking and any unreacted methyl tert butyl ether. If desired as a reaction product, a portion 140 of the isobutylene fraction may be recovered as a high purity isobutylene product fraction.

The oxygenate fraction 136, including methanol and methyl tert butyl ether, may be separated to recover the oxygenates, if desired. A first portion of the oxygenate fraction 136, which may be methanol or a mixture of methanol and methyl tert butyl ether, among other oxygenated reaction byproducts such as MSBE, and others noted above, may be returned via oxygenate fraction flow line 136 to etherification reaction zone 102. Additionally or alternatively, a second portion 138 of the oxygenate fraction may be used as startup or make-up selectivator in isobutylene dimerization unit 106, along with or in addition to any reaction modifier supplied from either the etherification unit 102 or oxygenate splitter 108.

Isobutylene fraction 134, or the portion not recovered as a high purity isobutylene product, is then mixed with a diluent 142 and fed to an isobutylene dimerization unit 106. Diluent 142 may include n-butane or isobutane, or a mixture of C4 paraffins, for example.

In the isobutylene dimerization unit, the isobutylene may be dimerized over a dimerization catalyst, and in the presence of the diluent and reaction moderator, at appropriate reaction conditions to form a dimerization reaction effluent comprising isooctene, reaction moderator, and byproduct isobutylene trimers and oligomers. The dimerization reaction effluent may then be separated to recover a heavy fraction 144 comprising isooctene, the byproduct isobutylene trimers and oligomers, methyl tert butyl ether, and methanol and a lights fraction 146 comprising isobutylene and methanol, as well as diluent n-butane or isobutane. If desired, the lights fraction 146 may be further processed to separate and recycle the methanol and the diluent to appropriate reaction units.

The heavy fraction 144 is fed to an oxygenate splitter to recover a first dimerization product fraction 148, comprising isooctene and the byproduct isobutylene trimers and oligomers, and a second dimerization product fraction 150 comprising reaction moderator. Reaction moderator may be recycled to the dimerization reaction zone 106 in some embodiments.

The first dimerization product fraction 148 is fed to a DIB purification unit 110. In the DIB purification unit 110, the first dimerization product fraction 148 is separated to recover an isooctene fraction 152, which may be a high purity isooctene fraction, such as comprising 95 wt % or greater isooctene, and a byproduct fraction 154 comprising the isobutylene trimers and oligomers.

As noted above, reaction zones herein may produce reaction byproducts. For example, one or both of the MTBE reaction effluent and the decomposition reaction effluent may further comprise one or more byproducts such as diisobutylene, methyl see butyl ether, tertiary butyl alcohol, or dimethyl ether, among others. Such components may travel with respective boiling point fractions recovered and processed as noted above.

Figure 2:
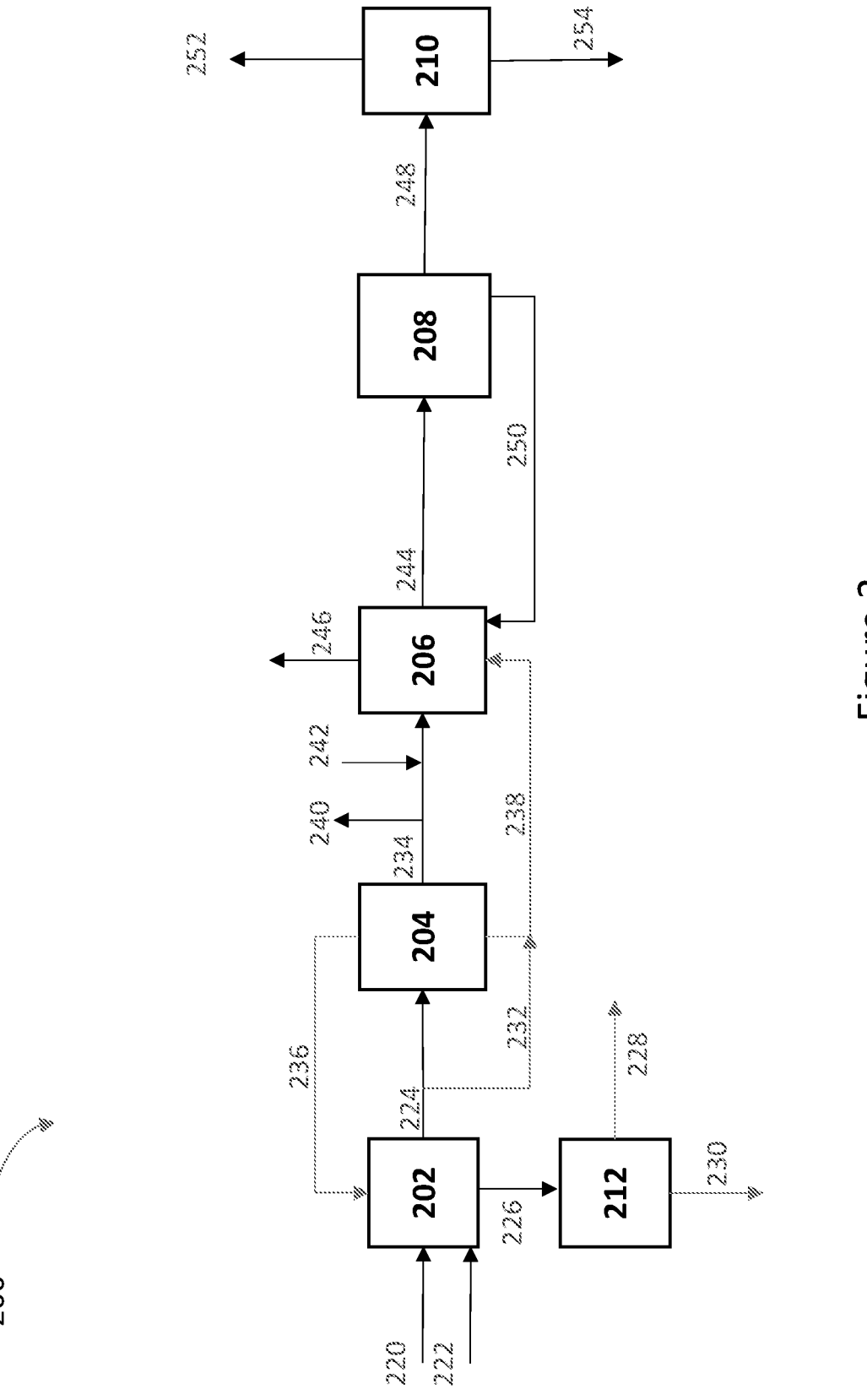

Referring now to FIG. 2, a simplified process flow diagram of a system 200 for producing high purity isobutylene and high purity isooctene according to embodiments herein is illustrated. System 200 may include primary unit operations including an ETBE conversion unit 202, an ETBE decomposition unit 204, an isobutylene dimerization unit 206, an oxygenate splitter 208, a diisobutylene purification zone 210, and an optional C4 separation zone 212. Each of these units may include, among other components, one or more of feed pretreatment equipment (filters, adsorbent beds, etc.), storage tanks, one or more reactors in series and/or parallel, separation units, which may include distillation columns, extractive distillation columns, flash drums, and/or strippers, and other components such as valves, pumps, controllers, overhead condensation systems (condensers, heat exchangers, drums, etc.), reboilers, etc. Not all units include each of these equipment. Further, while these components are not illustrated in the simplified process flow diagram, one skilled in the art can readily appreciate and understand the process flow and how such equipment may be incorporated as outlined in the following description.

Ethanol 220 and mixed C4 hydrocarbon stream 222 are fed to the ETBE conversion unit, which includes one or more reactors or catalytic distillation columns containing an etherification catalyst. The mixed C4 feed may include, for example, a mixture of hydrocarbons including 1-butene, 2-butene, n-butane, isobutane, and isobutylene. In the ETBE conversion unit, the feeds are contacted with the etherification catalyst at appropriate conditions for catalytically reacting isobutylene with ethanol to form ethyl tert butyl ether. An ETBE reaction effluent is recovered from the reaction zone(s), and the ETBE reaction effluent is then separated to recover a first fraction 224 comprising the ethyl tert butyl ether and a second fraction 226 comprising 1-butene, 2-butene, isobutane, and n-butane. In addition to recovering the ETBE and C4 products, ETBE conversion zone 202 may further include water wash columns, extractive distillation columns, and/or other separators for separating unreacted ethanol from the ETBE product, where the ethanol may be returned to the reactor for continued use in producing ETBE.

If it is desired to further process and separate the remaining C4 components in the second fraction, such as to recover 2-butene or isobutane, second fraction 226 may be fed to C4 separation zone 212. C4 separation zone 212 may include, for example, a distillation column or superfractionator to separate a heavy C4 fraction 228, including n-butane and 2-butene, from a light C4 fraction 230, including 1-butene, isobutane, and any unreacted isobutylene from the etherification reactor. In other embodiments, C4 separation zone 212 may include a catalytic deisobutenizer, which may include a positional isomerization catalyst zone for converting 1-butene to 2-butene and distillation structure or trays for separating a light C4 fraction 230, including isobutane and any unreacted isobutylene, from a heavy C4 fraction, including the 2-butene and n-butane.

First fraction 224, which includes the ethyl tert butyl ether produced in the etherification reactor, is then fed to an ETBE decomposition unit 204. For startup or as make-up oxygenate reaction moderator, a portion of the first fraction may be routed to isobutylene dimerization unit 206 via flow line 232.

In the ETBE decomposition unit, the ethyl tert butyl ether is decomposed (back cracked) to form a decomposition reaction effluent comprising isobutylene, ethanol, and unreacted ethyl tert butyl ether. The reaction effluent is then separated to recover an isobutylene fraction 234, which may be a high purity isobutylene stream, such as containing 95 wt % or greater isobutylene, and a first oxygenate fraction 236, which may include the ethanol resulting from the back cracking and any unreacted ethyl tert butyl ether. If desired as a reaction product, a portion 240 of the isobutylene fraction may be recovered as a high purity isobutylene product fraction.

The oxygenate fraction 236, including ethanol and ethyl tert butyl ether, may be separated to recover the oxygenates, if desired. A first portion of the oxygenate fraction 236, which may be ethanol or a mixture of ethanol and ethyl tert butyl ether, among other oxygenated reaction byproducts such as ESBE, DEE, and others noted above, may be returned via oxygenate fraction flow line 236 to etherification reaction zone 202. Additionally or alternatively, a second portion 238 of the oxygenate fraction may be used as startup or make-up selectivator in isobutylene dimerization unit 206, along with or in addition to any reaction modifier supplied from either the etherification unit 202 (via flow line 232) or oxygenate splitter 208 (via flow line 250).

Isobutylene fraction 234, or the portion not recovered as a high purity isobutylene product, is then mixed with a diluent 242 and fed to an isobutylene dimerization unit 206. Diluent 242 may include n-butane or isobutane or a mixture of C4 paraffins, for example.

In the isobutylene dimerization unit, the isobutylene may be dimerized over a dimerization catalyst, and in the presence of the diluent and reaction moderator, at appropriate reaction conditions to form a dimerization reaction effluent comprising isooctene, reaction moderator, and byproduct isobutylene trimers and oligomers. The dimerization reaction effluent may then be separated to recover a heavy fraction 244 comprising isooctene, the byproduct isobutylene trimers and oligomers, ethyl tert butyl ether, and ethanol and a lights fraction 246 comprising isobutylene and ethanol, as well as diluent n-butane or isobutane. If desired, the lights fraction 246 may be further processed to separate and recycle the ethanol and the diluent to appropriate reaction units.

The heavy fraction 244 is fed to an oxygenate splitter to recover a first dimerization product fraction 248, comprising isooctene and the byproduct isobutylene trimers and oligomers, and a second dimerization product fraction 250 comprising reaction moderator (oxygenates). The reaction moderator may be recycled to the dimerization reaction zone 206 in some embodiments.

The first dimerization product fraction 248 is fed to a DIB purification unit 210. In the DIB purification unit 210, the first dimerization product fraction 248 is separated to recover an isooctene fraction 252, which may be a high purity isooctene fraction, such as comprising 95 wt % or greater isooctene, and a byproduct fraction 254 comprising the isobutylene trimers and oligomers.

As noted above, reaction zones herein may produce reaction byproducts. For example, one or both of the ETBE reaction effluent and the decomposition reaction effluent may further comprise one or more byproducts such as diisobutylene, ethyl see butyl ether, tertiary butyl alcohol, or diethyl ether, among others. Such components may travel with respective boiling point fractions recovered and processed as noted above.

Figure 3:
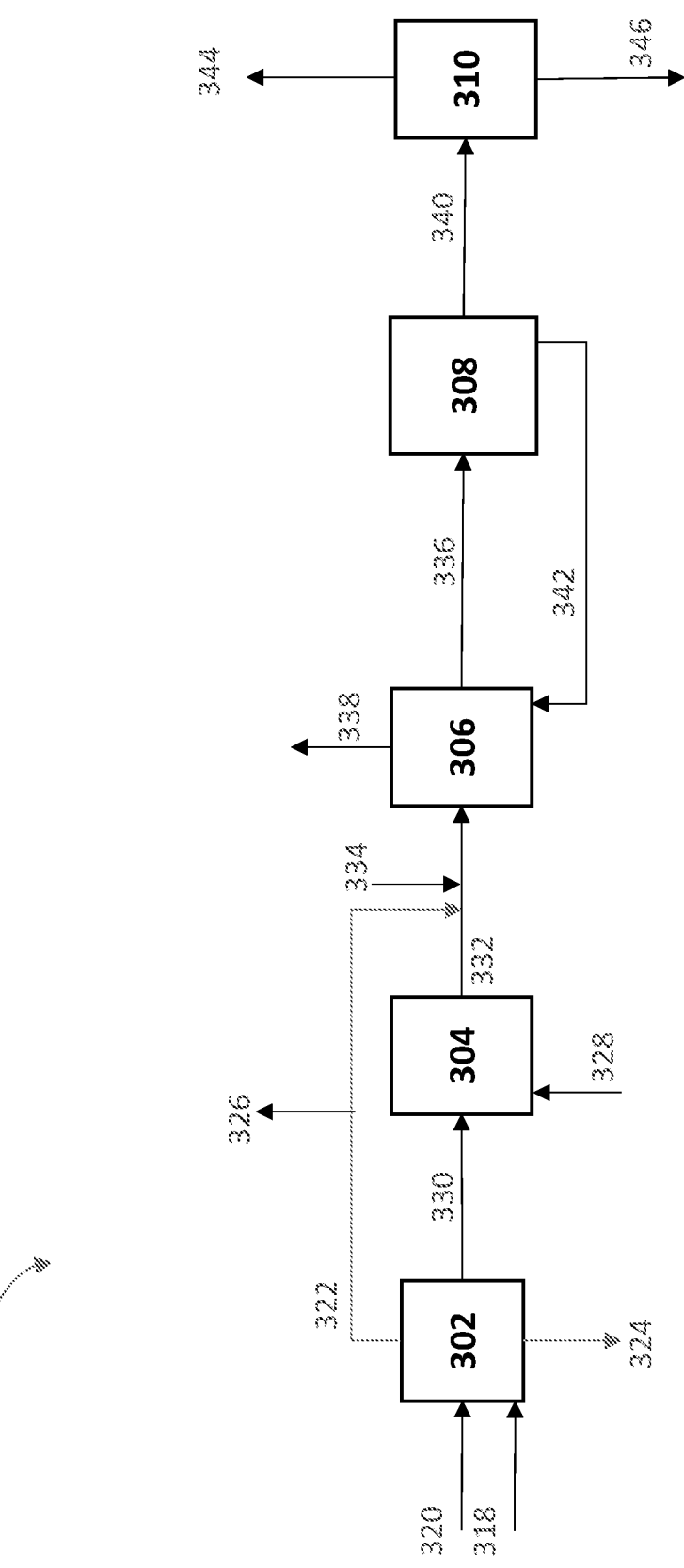

Referring now to FIG. 3, a simplified process flow diagram of a system 300 for producing high purity isobutylene and high purity isooctene according to embodiments herein is illustrated. System 300 may include primary unit operations including a C4 separation zone (deisobutenizer unit) 302, an etherification unit 304, an isobutylene dimerization unit 306, an oxygenate splitter 308, and a diisobutylene purification zone 310. Each of these units may include, among other components, one or more of feed pretreatment equipment (filters, adsorbent beds, etc.), storage tanks, one or more reactors in series and/or parallel, separation units, which may include distillation columns, extractive distillation columns, flash drums, and/or strippers, and other components such as valves, pumps, controllers, overhead condensation systems (condensers, heat exchangers, drums, etc.), reboilers, etc. Not all units include each of these equipment. Further, while these components are not illustrated in the simplified process flow diagram, one skilled in the art can readily appreciate and understand the process flow and how such equipment may be incorporated as outlined in the following description.

Hydrogen 318 and a mixed C4 stream 320, comprising a mixture of hydrocarbons including 1-butene, 2-butene, n-butane, isobutane, and isobutylene, are fed to a catalytic separation unit. Catalytic separation unit 302 may include a deisobutenizer and may optionally include an overhead splitter (not illustrated) or a side draw, each of which may be used to recover an isobutylene fraction or to further separate isobutane from isobutylene. For example, the mixture of hydrocarbons in the catalytic separation unit may be separated to recover a first overheads fraction comprising at least 95 wt % isobutylene and a side draw fraction comprising 1-butene, isobutane, and isobutylene, where the side draw fraction is fed as the isobutylene fraction fed to the etherification unit. Similarly, an overhead splitter may be used to further separate the isobutylene from isobutane, recovering a high purity isobutylene product and an isobutylene containing fraction fed to the etherification unit. The catalytic separation unit may also include a reactive distillation zone including a positional hydroisomerization catalyst for converting 1-butene to 2-butene, thus facilitating the separation of the close boiling C4 components to produce a high purity isobutylene fraction.

In the catalytic separation unit 302, a portion of the 1-butene is converted to 2-butene and the mixture of hydrocarbons is separated to recover a first overheads fraction 322 comprising isobutane, isobutylene, and any remaining 1-butene, and a bottoms fraction 324 comprising n-butane and 2-butene. If desired, a portion 326 of the first overheads fraction 322 may be recovered as a high purity isobutylene product fraction, such as a stream comprising at least 95 wt % isobutylene.

An alcohol stream 328, such as ethanol or methanol, and a second portion 330 of the first overheads fraction are fed to an etherification conversion unit 304. Second portion 330 of the isobutylene product is a minor portion of the isobutylene, which is used to generate an ether reaction modifier for use in the isobutylene dimerization unit 306, which receives the major portion of the isobutylene in the first overheads fraction 322.

In etherification conversion unit 304, alcohol and isobutylene are reacted to form an alkyl tert butyl ether, recovering an etherification reaction effluent 332, comprising alkyl tert butyl ether and unreacted alcohol, as well as various reaction byproducts, such as DEE, DME, TBA, ESBE, MSBE, or others noted above.

A diluent 334, such as isobutane or n-butane, and isobutylene in the first overheads fraction 322 are fed to isobutylene dimerization unit along with the etherification reaction effluent 332, which is fed to isobutylene dimerization unit 306 as a reaction moderator. In isobutylene dimerization unit 306, the isobutylene is dimerized to form a dimerization reaction effluent comprising isooctene, diluent, reaction moderator, and byproduct isobutylene trimers and oligomers. The dimerization reaction effluent is then separated to recover a heavy fraction 336 comprising isooctene, the byproduct isobutylene trimers and oligomers, alkyl tert butyl ether, and alcohol and a lights fraction 338 comprising diluent (isobutane or n-butane, for example), any unreacted isobutylene, and lighter reaction moderator, such as methanol or ethanol. If desired, the lights fraction 338 may be further processed to separate and recycle the alcohol and the diluent to appropriate reaction units.

The heavy fraction 336 is fed to an oxygenate splitter 308 to recover a first dimerization product fraction 340, comprising isooctene and the byproduct isobutylene trimers and oligomers, and a second dimerization product fraction 342, comprising reaction moderator. A portion or an entirety of second product fraction 342 may be returned to the isobutylene dimerization unit 306 for use as reaction moderator.

The first dimerization product fraction 340 is fed to a DIB purification unit 310. In DIB purification unit 310, the first dimerization product fraction 340 is separated to recover an isooctene fraction 344, which may be a high purity isooctene fraction, such as comprising 95 wt % or greater isooctene, and a byproduct fraction 346 comprising the isobutylene trimers and oligomers.

As outlined above, embodiments herein include various unit operations for producing and recovering the high purity isooctene and the high purity isobutylene. Such embodiments may include, for example, an etherification unit 30 (MTBE or ETBE production units), a catalytic separation unit (catalytic deisobutenizer), an ether decomposition unit (MTBE or ETBE decomposition units), an isobutylene dimerization unit, an oxygenates splitter, and a diisobutylene purification unit. Each of these units is described in more detail below.

Etherification Unit and Decomposition Units

The etherification followed by back-cracking reaction and separation scheme produces a high purity isobutylene product stream by selectively converting the isobutylene in the mixed C4 feed stream to one or more of methyl tert-butyl ether (MTBE), ethyl tert-butyl ether (ETBE) tertiary butyl alcohol (TBA), among other possible oxygenated intermediates, which allows for readily separating the resulting ether or alcohol from the lighter C4 n-olefins and paraffins. Back-cracking the ether or alcohol to form the constituent isobutene and water or alcohol then allows the isobutene to be easily separated from the water or alcohol and recovered as a high purity isobutylene product stream. The recovered alcohol or water may then be fed back into the reactor for selectively converting the isobutene.

The reaction system may include one or more reactors and catalytic distillation reactors suitable for etherification of the isobutene and one or more alcohols to form one or more C4 ethers, such as MTBE and/or ETBE. Alternatively, water may be used to convert the isobutene to an alcohol, such as TBA.

The C4 isoolefins may be processed according to embodiments herein to etherify the isoolefins. Catalysts used in reactors and distillation column reactors according to embodiments herein may have functionality to selectively hydrogenate butadiene, positionally isomerize olefins, and/or to etherify the isoolefins.

Typical conditions for the oxygenate reactions include catalyst bed temperatures above about 60° C. For catalytic distillation reactors, overhead pressures of above about 5.5 barg and equivalent liquid hourly space velocities of about 1.0 to 2.0 $hr^{-1}$ may be used. The temperature in the column is determined by the boiling point of the liquid mixture present at any given pressure. The temperature in the lower portions of the column will reflect the constitution of the material in that portion of the column, which will be higher than the overhead; that is, at constant pressure a change in the temperature indicates a change in the composition in the column. To change the temperature, the pressure in the column may be changed. Temperature control in the reaction zone is thus controlled by the pressure with the addition of heat (the reactions being exothermic) only causing more boil up. By increasing the pressure, the temperature is increased, and vice versa. Even though a distillation column reactor is used, some of the isoolefin may be unconverted and may exit the column with the overheads.

The ether product, being the highest boiling material, is removed from the distillation column reactor as a bottoms. The overheads may contain unreacted light alcohols, such as methanol or ethanol used in the upstream reactors as a reactant, and isoolefin along with light inerts, such as normal butenes and butanes.

The catalyst for the etherification may be any of known etherification catalysts such as an acidic cation exchange resin such as AMBERLYST 15 as supplied by DuPont Chemical Company. A suitable catalytic structure may be used herein to place the cation exchange resin particles into a bed within the fixed bed reactor. Further, the temperatures and pressures may be similar to those known in the art for performing the specified reactions.

In some embodiments, the etherification reaction system may include an unreacted n-butenes effluent. The effluent containing unreacted n-butenes from the oxygenate reaction unit may be fed to a C4 separation system. The C4 separation system may be used to produce an isobutane product stream, which may also contain isobutylene and/or 1-butene, and a normal butane plus 2-butenes product stream. These streams may be used as a diluent or hydrogenated to form a diluent paraffin stream in some embodiments. In some embodiments, the etherification reaction system may produce an ETBE product stream. In other embodiments, the etherification reaction system may produce a MTBE product stream.

The oxygenated (ether or alcohol) effluent from the etherification reaction system is then fed to a back-cracking unit. The back-cracking system produces high purity isobutene, along with unreacted feed components and reaction byproducts, such as n-butenes, tert-butyl alcohol (TBA), methanol or ethanol, unconverted MTBE or ETBE, methyl sec butyl ether (MSBE) or ethyl sec-butyl ether (ESBE), diethyl ether (DEE) or dimethyl ether (DME), or diisobutene (DIB). The back-cracking unit includes distillation units that separate the components in the reaction effluent to give high purity isobutylene. The recovered alcohol may be fed back to the etherification reaction system. In some embodiments, such as where the oxygenate is ethanol, the recovered ethanol may be fed back to the etherification reaction system to reduce the ethanol makeup. No additional external ethanol feed is required in some embodiments.

Contact of the ether feed with catalysts as described herein, at decomposition conditions, may result in the production of the desired olefin and alcohols, and byproducts, which may include by-product ethers, alcohols, and oligomers, such as a dimer or trimer of the desired olefin product. In some embodiments, contact of an ether feed with catalysts as described herein may result in conversion of at least 90 wt % of the ether; at least 85 wt % in other embodiments; at least 80 wt % in other embodiments; at least 75 wt % in other embodiments; and at least 70 wt % in other embodiments.

Figure 6:
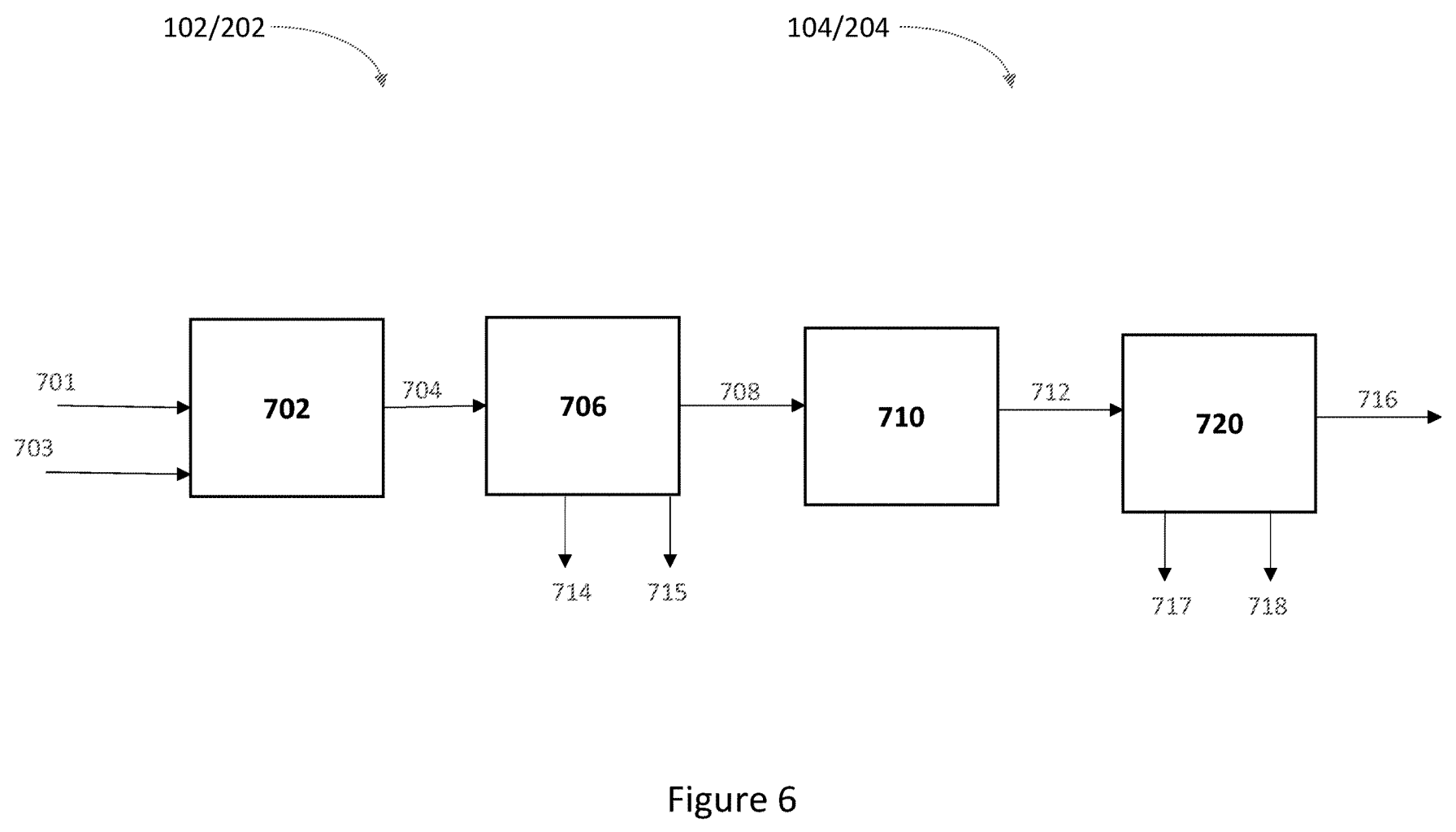

Referring now to FIG. 6, a simplified block flow diagram of an etherification unit (102, 202) plus a back-cracking unit (104, 204) according to embodiments herein is illustrated. A mixed C4 stream 701, including isobutylene among other components as described above, and a stream 703 containing an oxygenate reactant, such as methanol, ethanol, isobutanol, water, or a mixture thereof, may be fed to an etherification reaction system 702. Etherification reaction system 702 may include one or more reactors for selectively reacting, over an appropriate catalyst, the isobutylene with the water, methanol, ethanol, or other oxygenated reactant to form one or more of MTBE, ETBE, or TBA, for example. The reaction effluent 704 may then be fed to a separation system 706, which may include one or more distillation columns or extractive distillation columns, for example, to separate the MTBE, ETBE, or TBA from the unreacted C4 components in the mixed feed stream 701, recovering the MTBE, ETBE, or TBA as effluent stream 708, and recovering the lighter C4 components via one or more flow streams 714. Unreacted water or alcohol and other etherification reaction byproducts may be recovered by one or more flow streams 715.

The effluent stream 708 may then be fed to a back-cracking reaction system 710 for conversion of the MTBE, ETBE, or TBA back to the constituent molecules, isobutylene and the oxygenate reactant, such as water, methanol, or ethanol. Back-cracking reaction system 710 may include one or more reactors containing an appropriate back-cracking catalyst. Back cracked effluent 712 may then be recovered from the reactors and fed to separation system 720, which may include one or more distillation or extractive distillation columns for recovering a high purity isobutylene product 716, any heavy reaction byproducts 717, and the alcohol or water reactant 718, which can be recycled upstream to reaction system 702, if desired. While not illustrated, embodiments herein contemplate recovery of 1-butene, 2-butenes, MTBE, ETBE, or other components as a separate product stream from the various reaction effluents and separation schemes described above. Because the formation of the alcohol or the ether provides for efficient separation of the isobutylene from the n-butenes and isobutane that may be contained in the C4 feed streams, the use of etherification followed by back cracking may be used to produce a high purity isobutene product.

While the embodiment of FIG. 3 does not include a decomposition unit, the above description of the etherification unit applies to the embodiment of FIG. 3.

Dimerization Unit

Various catalysts and reactor configurations may be used for the selective dimerization of isobutylene to form isooctene. One example is the Isobutylene Dimerization process, which may selectively dimerize isobutylene to isooctene, where the reaction moderators may provide for selectively forming isooctene to dimers and trimers of isobutylene at a favorable ratio. Other known processes may also be used to dimerize the isobutylene to form isooctene according to embodiments herein. Byproducts including C9 and heavier components, such as trimers, tetramers, or other oligomers, as well as byproducts resulting from reaction of isobutylene with any reaction modifiers present may result in various heavier hydrocarbon species. Following dimerization of the isobutylene to form isooctene, the reaction effluent may be fed to a separation system for separation of the desired C8 olefins product stream from the C9 and heavier olefin byproducts.

Figure 5:
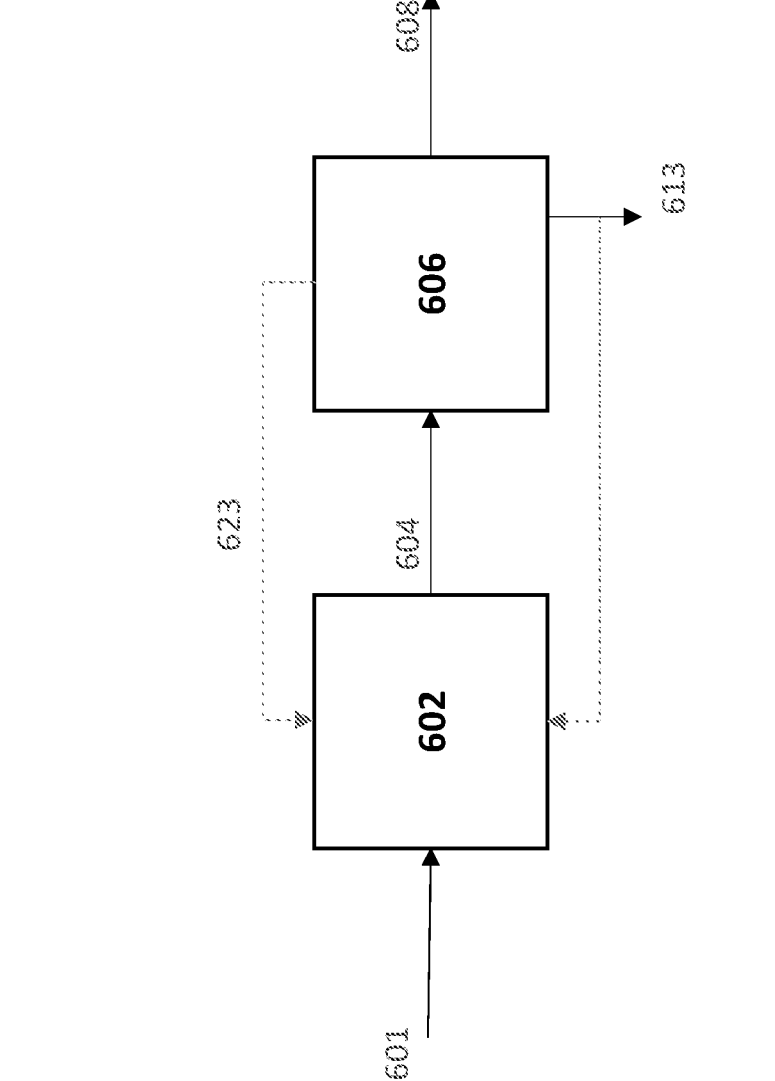
FIG. 5 illustrates a general process block flow diagram of isobutylene dimerization units according to one or more embodiments disclosed herein.

A general process block flow diagram of isobutylene dimerization units (106, 206, 306), according to embodiments herein, is illustrated in FIG. 5. An isobutylene containing stream 601 may be fed to an isobutylene dimerization reactor 602. Isobutylene dimerization reactor 302 may contain a selective dimerization catalyst and be operated at conditions suitable for dimerizing isobutylene (contained in stream 601) to produce isooctenes and various byproducts. The isobutylene dimerization reactor effluent may be recovered from the isobutylene dimerization reactor via flow stream 604, which may be fed to separation unit 606 for separating the raw isooctene product stream 608 from lighter components stream 613, such as unreacted isobutylene, diluent isobutane or n-butane, and any light reaction moderator. In some embodiments, such as where isobutylene conversion is incomplete, isobutylene may be stripped from the isooctenes produced, and may be purged or recycled via flow line 623 to the dimerization reactors for continued conversion. Similarly, any oxygenates, such as those recovered in stream 613, may be recycled to the dimerization reactor as a reaction moderator. Separation unit 606 may include, for example, one or multiple distillation or extractive distillation columns for performing the desired separations.

Oxygenate Splitter and Diisobutylene Purification Unit

Each of the oxygenate splitter unit and the diisobutylene purification units may include one or more distillation and or extractive distillation columns for the separation of the various components as described above. While additional details are not provided here, it is noted that for embodiments forming TBA as a byproduct, TBA forms an azeotrope with the C8 olefins, and to meet DIB purity requirements, TBA management is needed in the design of the oxygenate splitter with a purge stream.

C4 Separation Unit/CDDeIB Unit

As described in the embodiments above, a mixed C4 feed stream may be separated to recover a light C4 stream, such as including isobutylene, isobutane, and/or 1-butene, and a heavy C4 stream, including n-butane and 2-butene. In some embodiments, the C4 separation unit is or includes a catalytic deisobutenizer to fractionate the light (lower boiling) C4's from the heavy (higher boiling) C4's.

Figure 4:
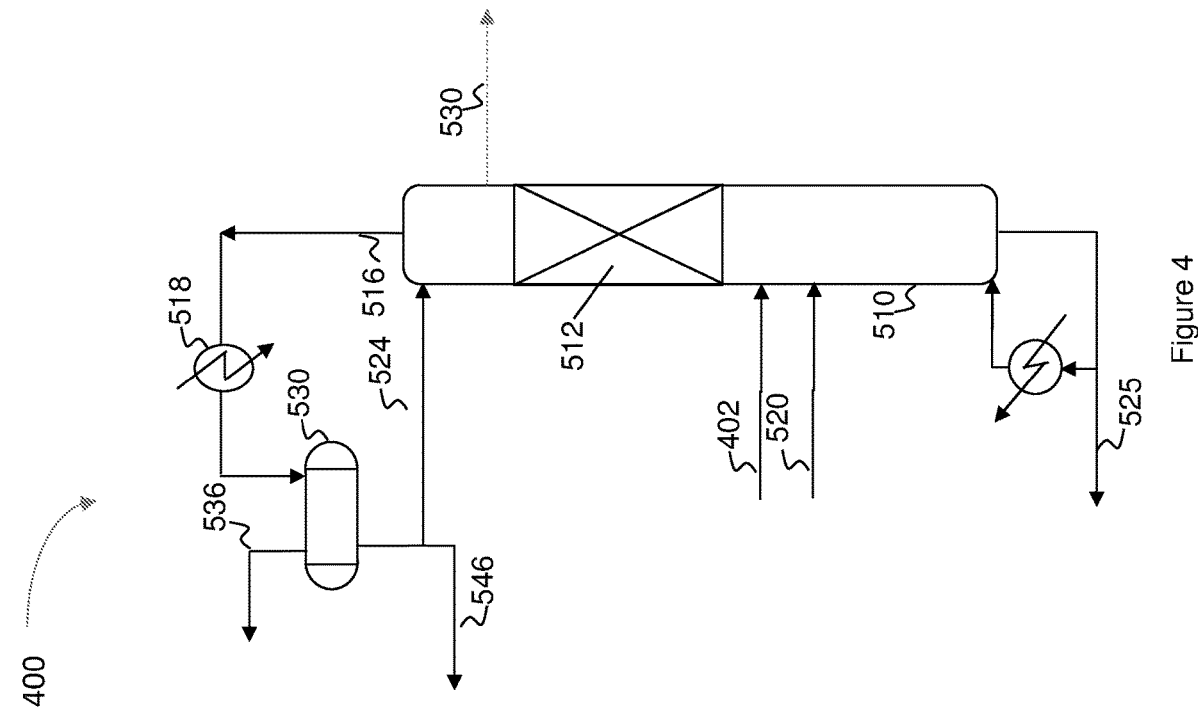
FIG. 4 illustrates a catalytic deisobutenizer useful in embodiments herein.

Referring now to FIG. 4, a simplified process flow diagram of catalytic deisobutenizer unit 400 according to embodiments herein is illustrated. The initial step is feeding a mixed C4 stream 402, such as the mixed C4 reaction effluent from the etherification unit (102, 202 from FIGS. 1 and 2, respectively) or a mixed C4 feed (320, FIG. 3), to a deisobutenizer (catalytic distillation column) 510. The mixed C4 stream containing 1-butene, 2-butene, isobutene and n-butane, among other possible C4 components, is fed to catalytic distillation column 510 near the bottom of a catalytic distillation section 512 (catalyst zone 512), which contains a supported hydroisomerization catalyst in the form of a catalytic distillation structure. Hydrogen may be fed via flow line 520, also introduced below the catalyst zone 512.

As the reactant feed contacts the catalyst, any butadiene in the feed is hydrogenated to butenes and equilibrium amounts of 1-butene and 2-butenes are produced at the catalyst. The 2-butene is distilled away and taken as bottoms, driving the reaction at the catalyst sites toward the production of 2-butenes.

The stripping section of the column may contain a conventional distillation structure, such as bubble cap, sieve trays or inert packing, to allow for complete separation of the 2-butenes product from the lower boiling isobutene and isobutane. Any normal butane present will also be removed as bottoms. The 2-butenes and normal butane may then be recovered from the catalytic distillation column 510 via flow line 525.

Overhead stream 516, including isobutane and any isobutylene and 1-butene, is condensed in condenser 518. The condensed overheads are collected in receiver separator 530, wherein the liquid isobutane and isobutylene are separated from hydrogen and light materials which are vented via flow line 536. The hydrogen may be recycled to the catalytic distillation column 510 if desired (recovery and recycle of hydrogen not illustrated). A portion of the condensed overhead product is recycled via flow line 524 to the catalytic distillation column 510 as reflux. The isobutane and isobutylene are removed as overheads product via flow line 546.

The overheads product stream 546 may include isobutylene as well as isobutane as may result from byproduct hydrogenation within the catalytic distillation column 510 or as a reaction byproduct elsewhere in the overall system (100, 200). In some embodiments, such as where a higher purity isobutylene product is desired, overheads product stream 546 may be fed to a splitter (not illustrated) for separation of the isobutylene from the isobutane. A small stripper may be required for trace isobutane removal, for example. In some embodiments, the deisobutenizer may be as described in U.S. Pat. No. 6,242,661 or U.S. Pat. No. 7,982,086. In other embodiments, an integrated isobutylene (IB) stripper, such as that described in U.S. Pat. No. 11,053,177, may be used to remove isobutane from the isobutylene, producing a higher purity isobutylene product.

The catalytic material employed for the isomerization reaction is preferably in a form to serve as distillation packing in such conventional distillation packing shapes as Raschig rings, Pall rings, saddles or the like and as such other structures as, for example, balls, irregular, sheets, tubes, spirals, packed in bags or other structures (such as those described in U.S. Pat. Nos. 4,242,530, 4,443,559, 5,189,001, 5,348,710, and 5,431,890), plated on grills or screens, or reticulated polymer foams (the cellular structure of the foams must be sufficiently large so as to not cause high pressure drops through the column, or otherwise arranged such as in chunks or concentration tubes to allow vapor flow). Similarly, the catalyst may be employed as palladium, platinum, or nickel supported on one-eighth inch alumina extrudates, either in bags or loosely packed in the column. In some embodiments, the catalyst may be contained in a structure as disclosed in U.S. Pat. Nos. 5,730,843, 5,266, 546, 4,731,229, and 5,073,236.

The catalyst contained in the reaction zone of the catalytic distillation column may be any catalyst suitable for the isomerization or hydroisomerization of 1-butene to 2-butenes. In some embodiments, the catalyst may contain palladium, platinum, or nickel, and may be in the form of an extrudate, for example. For hydroisomerization, the hydrogen rate to the distillation column reactor should be sufficient to maintain the catalyst in the active (hydride) form, as hydrogen is lost from the catalyst by hydrogenation when butadiene is contained in the feed. The hydrogen rate may be adjusted such that there is sufficient hydrogen to support the butadiene hydrogenation reaction and replace hydrogen lost from the catalyst but kept below that required for hydrogenation of butenes or to cause flooding of the column. Generally, the mole ratio of hydrogen to C4 hydrocarbon fed to the bed of catalytic distillation column will be in the range from about 0.01:1 to 0.60:1, preferably 0.01:1 to 0.10:1.

Embodiments herein may perform the catalytic distillation step in a catalyst packed column which can be appreciated to contain a vapor phase and some liquid phase, as in any distillation. Because the reaction is occurring concurrently with distillation, the initial reaction products are removed from the reaction zone as quickly as possible. Further, as all the components are boiling, the temperature of reaction is controlled by the boiling point of the mixture at the system pressure, which may vary from tray to tray. The heat of reaction simply creates more boil up but no increase in temperature. Additionally, the reaction has an increased driving force because the reaction products have been removed and cannot contribute to a reverse reaction. As a result, a great deal of control over the rate of reaction and distribution of products can be achieved by regulating the system pressure. Also, adjusting the throughput (residence time=liquid hourly space velocity 1) gives further control of product distribution and degree of 1-butene to 2-butenes conversion.

The temperature in the distillation column reactor is determined by the boiling point of the liquid mixture present at any given pressure. The temperature in the lower portions of the column will reflect the constitution of the material in that part of the column, and will be a higher temperature than the overhead; that is, at constant pressure a change in the temperature of the system indicates a change in the composition in the column. To change the temperature, the pressure is changed. Temperature control in the reaction zone is thus effected by a change in pressure; by increasing the pressure, the temperature in the system is increased, and vice versa.

The catalytic distillation column according to embodiments herein may be operated at an overhead temperature in the range of 32° C. to 138° C. and at pressures in the range of 3 bara to 20 bara, bearing in mind the effect of pressure on temperature as discussed above. In other embodiments, the catalytic distillation column according to embodiments herein may be operated at an overhead temperature in the range of 85° C. or 90° C. to 130° C. or 135° C. and at pressures in the range of 9 bara, 10 bara, or 11 bara to 16 bara, 18 bara, or 20 bara, where any lower limit may be combined with any upper limit. In other embodiments, the overhead temperature of the catalytic distillation column may be in the range from 32° C. to about 80° C., such as from about 47° C. to about 68° C., or from about 60° C. to about 65° C. In yet other embodiments, the overhead temperature may be in the range from a lower limit of 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85 or 90° C. to an upper limit of 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 100, 110, 120, 130, or 138° C., where any lower limit may be combined with any upper limit. In some embodiments, the overhead pressure of the catalytic distillation column may be in the range from about 3 bara to about 12 bara, such as in the range from about 7 bara to about 10 bara. In yet other embodiments, the overhead pressure of the catalytic distillation column may be in the range from a lower limit of about 9, 10, 11, 12, 13, 14, or 15 bara to an upper limit of about 14, 15, 16, 17, 18, 19, or 20 bara. Bottoms temperatures of the catalytic distillation column will correspond to the boiling point of the higher boiling components at the operating conditions, and in various embodiments, may be in the range from about 60° C. to about 180° C., such as from about 60° C. to about 100° C., or from about 65° C. to about 88° C., for example, but may also be higher based on the desired overhead temperature and pressure. The temperature of operation may also take into consideration the activity of the catalyst for promoting the desired 1-butene to 2-butenes reaction.

In embodiments herein, the catalytic distillation column is operated under conditions, particularly temperature and pressure, which tend to exclude 2-butenes from contact with the catalyst while holding the 1-butene in contact with the catalyst. Thus, as 1-butene is isomerized to 2-butenes, it drops down in the column away from the catalyst and is removed as bottoms. The column may include a reflux, where the reflux ratio may be in the range from 0.5:1 to 33:1, for example.

As described above, the mixed C4s are fed to a catalytic distillation column. In the catalytic distillation column, the C4 stream is further processed using positional isomerization and hydrogenation catalysts, along with a hydrogen feed, converting 1-butene to 2-butenes and selectively hydrogenating any butadiene that may be present from upstream processing. Concurrent fractionation results in two C4 product streams in some embodiments, including a 2-butenes and n-butane bottoms product and a high purity isobutene overhead product. A hydrogen containing vent gas may also be recovered.

With respect to FIG. 3, isobutylene product streams produced from processing of the C4 feed through a catalytic distillation column may have an isobutylene content of at least 80 wt %. High purity isobutylene product streams may be produced, having a purity of at least 85 wt %, at least 90 wt %, at least 95 wt %, at least 98 wt %, at least 99 wt %, at least 99.5 wt %, or at least 99.9 wt % in various embodiments. With respect to FIGS. 1 and 2, the C4 fraction fed to the C4 separation zone may be lean in isobutylene, as reacted away in the etherification reaction zone; in such instances, the overhead product from the catalytic distillation may be a high purity isobutane product, having a purity of at least 85 wt %, at least 90 wt %, at least 95 wt %, at least 98 wt %, at least 99 wt %, at least 99.5 wt %, or at least 99.9 wt % in various embodiments.

In still other embodiments, catalytic distillation columns for processing mixed C4 streams herein may result in three C4-product streams, including a 2-butenes and n-butane bottoms product, an isobutane overhead product, and a high purity isobutylene product. The high purity isobutylene product may be recovered, for example, as a bottoms draw from a splitter, as noted above, or in some embodiments may be recovered as a side draw fraction 530 from the catalytic distillation column. The side draw may be located within the column at an appropriate elevation to recover an isobutane/isobutene stream having a ratio of isobutane to isobutene in the range from 0.001:1 to 2:1, such as 0.01:1 to 1:1.5, or from 0.1:1 to 1:1 for example. The side draw may be located above the catalytic distillation reaction zone, and the feed may be located below the catalytic distillation reaction zone, providing for a side draw containing a relatively low amount of n-butenes, such that a stream containing greater than 80%, greater than 95%, greater than 98%, or greater than 99%, or greater than 99.9% isobutylene may be recovered. Sufficient trays and height to the column may also be provided to result in an isobutane overhead stream containing primarily isobutane, such as greater than 95% or greater than 98% isobutane (each in wt %).

In some embodiments, due to the isomerization of 1-butene to 2-butene within the catalytic distillation column, isobutylene product streams produced herein, whether an overhead or a side draw from the catalytic distillation column, may have a purity of at least 99.9 wt %, 99.95 wt %, or 99.99 wt % isobutylene based on a total amount of isobutylene and 1-butene contained in the high purity isobutylene product stream.

Diluent

It has been found that operation of the isobutylene dimerization unit is improved with addition of diluent. The n-butanes, produced in the catalytic distillation column unit (FIG. 3), or recovered in the etherification unit of C4 separation unit (FIGS. 1 and 2), may be fed into the dimerization unit, where the n-butane may act as a diluent to help control the reaction within the skeletal isomerization unit. Alternatively, fresh or make-up butanes may be provided to the dimerization unit. In some instances, such as in embodiments where the feed concentration or formation of n-butane by-product is low, the resulting diluent feed to the dimerization unit would also have a low amount of n-butane. In such embodiments, a saturation (hydrogenation) reactor may be used to react n-butenes with hydrogen to form a desired amount of n-butane for use as a diluent during skeletal isomerization.

Dehydrogenation

If present at sufficient quantities, a recovered isobutane product may be dehydrogenated to form additional isobutene and hydrogen, if desired. The hydrogen may be recovered and used as a feed to the catalytic deisobutenizer or the hydrogenation reactor to generate n-butane diluent, while the C4 dehydrogenation effluent may be fed to the catalytic deisobutenizer, the etherification reactor, or otherwise processed using process units herein to recover the additional isobutylene.

As described above, embodiments herein include the production of MTBE or ETBE for use as a dimerization moderator to produce isooctene and isobutylene at high purity via ether back cracking. Based on enthalpy calculations between ETBE and MTBE decomposition, the enthalpy from ETBE decomposition is lower than MTBE, and hypothetically means it requires lesser energy. Hypothetically, the same reactor conditions in MTBE decomposition mode can also be applied in ETBE decomposition based on enthalpy data from the in-house model for compounds. In terms of decomposition rate between ETBE and MTBE, a 5% lower decomposition rate is estimated. For an MTBE decomp rate of 88%, ETBE is assumed to be 95% of 88% which is around 84%. The expected components at the outlet of the isobutylene reactor in ETBE environment are isobutylene, n-butenes, TBA, ethanol, unconverted ETBE and ESBE, DEE (heavier than DME) and DIB. These components can be separated by distillation to purify the isobutylene product. The recovered ethanol from the decomposition process can be fed back to the upstream etherification unit to reduce the ethanol make-up from the source. From the ETBE reaction process, the resulting components such as ETBE, ESBE, TBA, DIB, DEE, water, and additional ethanol can then be used as moderator for the subsequent dimerization step to produce isooctene. The purity of the isooctene will depend on the amount of n-butenes present in the feed, which in some embodiments is less than 1 wt %. The lesser the n-butenes present in the C4 feed, the higher the purity of the final isooctene (DIB) product will be. Variations in the dimerization selectivators can also be used; ethanol derived oxygenates can be used as well as C1 to C4 alcohols and or glycol.

The schemes illustrated and described herein may be used for the conversion of existing MTBE Units (for example) for gasoline blending and convert such units to produce isooctene for petrochemical applications. The scheme can also be used for co-production of HPIB and HPDIB. Advantages of the schemes herein is the possible reuse of existing MTBE platforms for the isooctene process and having a semi-closed loop system in the use of external diluents.

Reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors. Reactors useful in embodiments disclosed herein may be used as a stand-alone reactor or may be used in combination with one or more reactors of the same or different type.

Any type of reactor may be used to carry out the reactions described herein. The examples of reactors suitable for carrying out the reactions of embodiments herein may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, conventional fixed bed reactors, or any combination of these reactors. Multiple-reactor systems useful in embodiments disclosed herein may include a series of the same type of reactor or reactors in parallel, or different types of reactors in series, for the respective reaction zones. A person of ordinary skill in the art would recognize that other types of reactors may also be used.

Unless defined otherwise, all technical and scientific terms used have the same meaning as commonly understood by one of ordinary skill in the art to which these systems, apparatuses, methods, processes, and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

When the word "approximately" or "about" are used, this term may mean that there can be a variance in value of up to +10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed as new and desired to be protected by Letters Patent is:

1. A process for co-production of high purity isobutylene and high purity isooctene, the process comprising:
   feeding ethanol and mixed C4 hydrocarbon to an ETBE conversion unit, the mixed C4 feed containing a mixture of hydrocarbons including 1-butene, 2-butene, n-butane, isobutane, and isobutylene;
   in the ETBE conversion unit, catalytically reacting the isobutylene with the ethanol to form ethyl tert butyl ether, recovering an ETBE reaction effluent, and separating the ETBE reaction effluent to recover a first fraction comprising the ethyl tert butyl ether and a second fraction comprising 1-butene, 2-butene, isobutane, and n-butane;
   feeding the first fraction comprising the ethyl tert butyl ether to an ETBE decomposition unit;
   in the ETBE decomposition unit, decomposing ethyl tert butyl ether to form a decomposition reaction effluent comprising isobutylene, ethanol and unreacted ethyl tert butyl ether, and separating the reaction effluent to recover an isobutylene fraction, comprising 95 wt % or greater isobutylene, and a first oxygenate fraction comprising the ethanol and unreacted ethyl tert butyl ether;
   recovering a first portion of the isobutylene fraction as a high purity isobutylene product fraction;
   feeding a second portion of the isobutylene fraction to an isobutylene dimerization unit;
   feeding a portion of the first fraction comprising ethyl tert butyl ether, a portion of the first oxygenate fraction, or both, to the isobutylene dimerization unit as a reaction moderator;
   in the isobutylene dimerization unit, dimerizing the isobutylene to form a dimerization reaction effluent comprising isooctene, reaction moderator, and byproduct isobutylene trimers and oligomers, and separating the dimerization reaction effluent to recover a heavy fraction comprising isooctene, the byproduct isobutylene trimers and oligomers, ethyl tert butyl ether, and ethanol and a lights fraction comprising isobutylene and ethanol;
   feeding the heavy fraction to an oxygenate splitter to recover a first dimerization product fraction comprising isooctene and the byproduct isobutylene trimers and oligomers and a second dimerization product fraction comprising reaction moderator;
   feeding the first dimerization product fraction to a DIB purification unit; and
   in the DIB purification unit, separating the first dimerization product fraction to recover an isooctene fraction, comprising 95 wt % or greater isooctene, and a byproduct fraction comprising the isobutylene trimers and oligomers.

2. The process of claim 1, further comprising feeding a portion of the second dimerization product fraction comprising the reaction moderator to the isobutylene dimerization unit as additional reaction moderator.

3. The process of claim 1, further comprising feeding the second fraction to a C4 separation unit, and in the C4 separation unit separating the second fraction to recover a light C4 fraction comprising 1-butene and isobutane and a heavy C4 fraction comprising 2-butene and n-butane.

4. The process of claim 1, wherein one or both of the ETBE reaction effluent and the decomposition reaction effluent further comprise one or more byproducts diisobutene, ethyl sec butyl ether, tertiary butyl alcohol, or diethyl ether.

5. The process of claim 1, further comprising feeding a portion of the first oxygenate fraction to the ETBE conversion unit.

6. A process for co-production of high purity isobutylene and high purity isooctene, the process comprising:
   feeding methanol and mixed C4 hydrocarbon to a MTBE conversion unit, the mixed C4 feed containing a mixture of hydrocarbons including 1-butene, 2-butene, n-butane, isobutane, and isobutylene;
   in the MTBE conversion unit, catalytically reacting isobutylene with methanol to form methyl tert butyl ether, recovering an MTBE reaction effluent, and separating the MTBE reaction effluent to recover a first fraction comprising the methyl tert butyl ether and a second fraction comprising 1-butene, 2-butene, isobutane, and n-butane;

feeding the first fraction comprising the methyl tert butyl ether to an MTBE decomposition unit;

in the MTBE decomposition unit, decomposing methyl tert butyl ether to form a decomposition reaction effluent comprising isobutylene, methanol and unreacted methyl tert butyl ether, and separating the reaction effluent to recover an isobutylene fraction, comprising 95 wt % or greater isobutylene, and a first oxygenate fraction comprising the methanol and unreacted methyl tert butyl ether;

recovering a first portion of the isobutylene fraction as a high purity isobutylene product fraction;

feeding a second portion of the isobutylene fraction to an isobutylene dimerization unit;

feeding a portion of the first fraction comprising methyl tert butyl ether, a portion of the first oxygenate fraction, or both, to the isobutylene dimerization unit as a reaction moderator;

in the isobutylene dimerization unit, dimerizing the isobutylene to form a dimerization reaction effluent comprising isooctene, reaction moderator, and byproduct isobutylene trimers and oligomers, and separating the dimerization reaction effluent to recover a heavy fraction comprising isooctene, the byproduct isobutylene trimers and oligomers, methyl tert butyl ether, and methanol and a lights fraction comprising isobutylene and methanol;

feeding the heavy fraction to an oxygenate splitter to recover a first dimerization product fraction comprising isooctene and the byproduct isobutylene trimers and oligomers and a second dimerization product fraction comprising reaction moderator;

feeding the first dimerization product fraction to a DIB purification unit; and in the DIB purification unit, separating the first dimerization product fraction to recover an isooctene fraction, comprising 95 wt % or greater isooctene, and a byproduct fraction comprising the isobutylene trimers and oligomers.

7. The process of claim 6, further comprising feeding a portion of the second dimerization product fraction comprising the reaction moderator to the isobutylene dimerization unit as additional reaction moderator.

8. The process of claim 6, further comprising feeding the second fraction to a C4 separation unit, and in the C4 separation unit separating the second fraction to recover a light C4 fraction comprising 1-butene and isobutane and a heavy C4 fraction comprising 2-butene and n-butane.

9. The process of claim 6, wherein one or both of the MTBE reaction effluent and the decomposition reaction effluent further comprise one or more byproducts diisobutene, methyl sec butyl ether, tertiary butyl alcohol, or dimethyl ether.

10. The process of claim 6, further comprising feeding a portion of the first oxygenate fraction to the MTBE conversion unit.

11. A process for co-production of high purity isobutylene and high purity isooctene, the process comprising:

feeding a mixed C4 stream, comprising a mixture of hydrocarbons including 1-butene, 2-butene, n-butane, isobutane, and isobutylene, to a catalytic separation unit;

in the catalytic separation unit, converting a portion of the 1-butene to 2-butene and separating the mixture of hydrocarbons to recover a first overheads fraction comprising 1-butene, isobutane, and isobutene and a bottoms fraction comprising n-butane and 2-butene;

recovering a portion of the first overheads fraction as a high purity isobutylene product fraction comprising at least 95 wt % isobutylene;

feeding an alcohol, selected from ethanol or methanol, and a second portion of the first overheads fraction to an etherification conversion unit;

in the etherification conversion unit, reacting alcohol and isobutylene to form an alkyl tert butyl ether, recovering an etherification reaction effluent comprising alkyl tert butyl ether and alcohol;

feeding the etherification reaction effluent to an isobutylene dimerization unit as a reaction moderator;

feeding a second portion of the first overheads fraction to the isobutylene dimerization unit;

in the isobutylene dimerization unit, dimerizing the isobutylene to form a dimerization reaction effluent comprising isooctene, reaction moderator, and byproduct isobutylene trimers and oligomers, and separating the dimerization reaction effluent to recover a heavy fraction comprising isooctene, the byproduct isobutylene trimers and oligomers, alkyl tert butyl ether, and alcohol and a lights fraction comprising isobutylene and alcohol;

feeding the heavy fraction to an oxygenate splitter to recover a first dimerization product fraction comprising isooctene and the byproduct isobutylene trimers and oligomers and a second dimerization product fraction comprising reaction moderator;

feeding the first dimerization product fraction to a DIB purification unit; and in the DIB purification unit, separating the first dimerization product fraction to recover an isooctene fraction, comprising 95 wt % or greater isooctene, and a byproduct fraction comprising the isobutylene trimers and oligomers.

12. The process of claim 11, wherein separating the mixture in the catalytic separation unit comprises recovering a first overheads fraction comprising at least 95 wt % isobutylene and a side draw fraction comprising 1-butene, isobutane, and isobutylene, and wherein the side draw fraction is fed as the second fraction provided to the etherification conversion unit.

13. The process of claim 11, further comprising feeding a portion of the second dimerization product fraction to the isobutylene dimerization unit.

14. The process of claim 11, wherein the alcohol is ethanol.

15. The process of claim 11, wherein the alcohol is methanol.

16. A system for co-production of high purity isobutylene and high purity isooctene, the system comprising:

one or more flow conduits for providing ethanol and mixed C4 hydrocarbon to an ETBE conversion unit, the mixed C4 hydrocarbon containing a mixture of hydrocarbons including 1-butene, 2-butene, n-butane, isobutane, and isobutylene;

the ETBE conversion unit, including one or more reactors configured for catalytically reacting the isobutylene with the ethanol to form ethyl tert butyl ether, recovering an ETBE reaction effluent, and a separation system configured for separating the ETBE reaction effluent to recover a first fraction comprising the ethyl tert butyl ether and a second fraction comprising 1-butene, 2-butene, isobutane, and n-butane;

a flow line for feeding the first fraction comprising the ethyl tert butyl ether to an ETBE decomposition unit;

the ETBE decomposition unit, including one or more reactors configured for decomposing ethyl tert butyl ether to form a decomposition reaction effluent comprising isobutylene, ethanol and unreacted ethyl tert butyl ether, and a separation system configured for separating the reaction effluent to recover an isobutylene fraction, comprising 95 wt % or greater isobutylene, and a first oxygenate fraction comprising the ethanol and unreacted ethyl tert butyl ether;

a flow line for recovering a first portion of the isobutylene fraction as a high purity isobutylene product fraction;

a flow line for feeding a second portion of the isobutylene fraction to an isobutylene dimerization unit;

a flow line for feeding a portion of the first fraction comprising ethyl tert butyl ether, a portion of the first oxygenate fraction, or both, to the isobutylene dimerization unit as a reaction moderator;

the isobutylene dimerization unit, including one or more reactors configured for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, ethyl tert butyl ether, and ethanol and a lights fraction comprising isobutylene and ethanol;

an oxygenate splitter for separating the heavy fraction to recover a first dimerization product fraction comprising isooctene and the byproduct isobutylene trimers and oligomers and a second dimerization product fraction comprising reaction moderator;

a flow line for feeding the first dimerization product fraction to a DIB purification unit; and the DIB purification unit, including a separation system for separating the first dimerization product fraction to recover an isooctene fraction, comprising 95 wt % or greater isooctene, and a byproduct fraction comprising the isobutylene trimers and oligomers.

17. A system for co-production of high purity isobutylene and high purity isooctene, the system comprising:

one or more flow conduits for providing methanol and mixed C4 hydrocarbon to a MTBE conversion unit, the mixed C4 hydrocarbon containing a mixture of hydrocarbons including 1-butene, 2-butene, n-butane, isobutane, and isobutylene;

the MTBE conversion unit, including one or more reactors configured for catalytically reacting isobutylene with methanol to form methyl tert butyl ether, recovering an MTBE reaction effluent, and a separation system for separating the MTBE reaction effluent to recover a first fraction comprising the methyl tert butyl ether and a second fraction comprising 1-butene, 2-butene, isobutane, and n-butane;

a flow line for feeding the first fraction comprising the methyl tert butyl ether to an MTBE decomposition unit;

the MTBE decomposition unit, including one or more reactors for decomposing methyl tert butyl ether to form a decomposition reaction effluent comprising isobutylene, methanol and unreacted methyl tert butyl ether, and a separation system configured for separating the reaction effluent to recover an isobutylene fraction, comprising 95 wt % or greater isobutylene, and a first oxygenate fraction comprising the methanol and unreacted methyl tert butyl ether;

a flow line for recovering a first portion of the isobutylene fraction as a high purity isobutylene product fraction;

a flow line for feeding a second portion of the isobutylene fraction to an isobutylene dimerization unit;

a flow line for feeding a portion of the first fraction comprising methyl tert butyl ether, a portion of the first oxygenate fraction, or both, to the isobutylene dimerization unit as a reaction moderator;

the isobutylene dimerization unit, including one or more reactors for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, methyl tert butyl ether, and methanol and a lights fraction comprising isobutylene and methanol;

an oxygenate splitter for separating the heavy fraction to recover a first dimerization product fraction comprising isooctene and the byproduct isobutylene trimers and oligomers and a second dimerization product fraction comprising reaction moderator;

a flow line for feeding the first dimerization product fraction to a DIB purification unit; and the DIB purification unit, including a separation system for separating the first dimerization product fraction to recover an isooctene fraction, comprising 95 wt % or greater isooctene, and a byproduct fraction comprising the isobutylene trimers and oligomers.

18. A system for co-production of high purity isobutylene and high purity isooctene, the system comprising:

one or more flow lines for feeding a mixed C4 stream, comprising a mixture of hydrocarbons including 1-butene, 2-butene, n-butane, isobutane, and isobutylene, to a catalytic separation unit;

the catalytic separation unit, comprising a catalytic distillation column configured for concurrently converting a portion of the 1-butene to 2-butene and separating the mixture of hydrocarbons to recover a first overheads fraction comprising 1-butene, isobutane, and isobutene and a bottoms fraction comprising n-butane and 2-butene;

a flow line for recovering a portion of the first overheads fraction as a high purity isobutylene product fraction comprising at least 95 wt % isobutylene;

one or more flow lines for feeding an alcohol, selected from ethanol or methanol, and a second portion of the first overheads fraction to an etherification conversion unit;

the etherification conversion unit, including one or more reactors for reacting alcohol and isobutylene to form an alkyl tert butyl ether, recovering an etherification reaction effluent comprising alkyl tert butyl ether and alcohol;

a flow line for feeding the etherification reaction effluent to an isobutylene dimerization unit as a reaction moderator;

a flow line for feeding a second portion of the first overheads fraction to the isobutylene dimerization unit;

the isobutylene dimerization unit, including one or more reactors for dimerizing the isobutylene to form a dimerization reaction effluent comprising isooctene, reaction moderator, and byproduct isobutylene trimers and oligomers, and a separation system for separating the dimerization reaction effluent to recover a heavy fraction comprising isooctene, the byproduct isobutylene trimers and oligomers, alkyl tert butyl ether, and alcohol and a lights fraction comprising isobutylene and alcohol;

an oxygenate splitter for separating the heavy fraction to recover a first dimerization product fraction comprising isooctene and the byproduct isobutylene trimers and oligomers and a second dimerization product fraction comprising reaction moderator;

a flow line for feeding the first dimerization product fraction to a DIB purification unit; and the DIB purification unit, including a separation system for separating the first dimerization product fraction to recover an isooctene fraction, comprising 95 wt % or greater isooctene, and a byproduct fraction comprising the isobutylene trimers and oligomers.

\* \* \* \* \*